(12) United States Patent
Leedham et al.

(10) Patent No.: US 6,383,669 B1
(45) Date of Patent: May 7, 2002

(54) CHEMICAL VAPOR DEPOSITION PRECURSORS

(75) Inventors: Timothy J Leedham, Diss Norfolk; Anthony C Jones, Prescot; Michael J Crosbie, Malvern; Dennis J Williams, Malvern; Peter J Wright, Malvern; Penelope A Lane, Malvern, all of (GB)

(73) Assignee: The Secretary of State for Defence in Her Britannic Majesty's Government of the United Kingdom of Great Britain and Northern Ireland, Farnborough (GB)

( * ) Notice: Subject to any disclaimer, the term of this patent is extended or adjusted under 35 U.S.C. 154(b) by 0 days.

(21) Appl. No.: 09/423,750

(22) PCT Filed: May 13, 1998

(86) PCT No.: PCT/GB98/01365

§ 371 Date: Dec. 1, 1999

§ 102(e) Date: Dec. 1, 1999

(87) PCT Pub. No.: WO98/51837

PCT Pub. Date: Nov. 19, 1998

(30) Foreign Application Priority Data

May 14, 1997 (GB) .............................................. 9709639

(51) Int. Cl.[7] .............................. B05D 5/12; C23C 16/06; C07F 7/00
(52) U.S. Cl. ..................... 428/702; 427/124; 427/126.3; 427/252.32; 556/40; 556/54; 428/446
(58) Field of Search ................................. 427/123–125, 427/126.3, 126.5, 79, 255.32; 556/40, 54; 428/446, 702

(56) References Cited

U.S. PATENT DOCUMENTS

| | | | | |
|---|---|---|---|---|
| 5,280,012 A | * | 1/1994 | Kirlin et al. | 505/1 |
| 5,343,353 A | * | 8/1994 | Miki et al. | 361/322 |
| 5,677,002 A | * | 10/1997 | Kirlin et al. | 427/248.1 |
| 5,840,897 A | * | 11/1998 | Kirlin et al. | 546/2 |

FOREIGN PATENT DOCUMENTS

| | | | |
|---|---|---|---|
| WO | WO 93/18202 A1 | * | 9/1993 |
| WO | 40690 | * | 12/1996 |
| WO | WO 96/40690 A1 | * | 12/1996 |

* cited by examiner

Primary Examiner—Brian K. Talbot
(74) Attorney, Agent, or Firm—Nixon & Vanderhye

(57) ABSTRACT

Zirconium precursors for use in depositing thin films of or containing zirconium oxide using an MOCVD technique have the following general formula: $Zr_x(OR)_yL$, wherein R is an alkyl group; L is a β-diketonate group; x=1 or 2; y=2, 4 or 6; and z=1 or 2.

22 Claims, 8 Drawing Sheets

CHEMICAL VAPOR DEPOSITION PRECURSORS

This application is a 35 U.S.C. §371 national phase entry of PCT/GB98/01365 filed May 13, 1998.

DESCRIPTION

This invention concerns precursors for use in chemical vapour deposition techniques the production of electro-ceramic devices therefrom, and their use in ferro-electric memories and I.R. detectors.

Metalorganic chemical vapour deposition (MOCVD) is a preferred method for depositing thin films, i.e. in the order of a few Am of ferroelectric metal oxides, such as lead zirconate titanate, [Pb(Zr,Ti)O$_3$ or PZT and lanthanum-modified lead zirconate titanate. [(Pb,La)(Zr,Ti)O$_3$ or PLZT]. These electro-ceramic materials have a wide range of useful dielectric, ferroelectric, piezoelectric, pyroelectric and electrostrictive properties, giving rise to a variety of potential applications ranging from thermal imaging and security systems to integrated optics and computer memories, e.g. DRAMS and non-volatile FERAMS.

The MOCVD technique involves transporting a metal as a volatile metalorganic compound in the vapour phase followed by thermal decomposition usually in the presence of oxygen on an appropriate substrate. The different types of substrate can be divided into three groups, namely oxides, semiconductors and metals. Examples of suitable oxide substrates are SiO2, SrTiO$_3$, MgO and Al$_2$O$_3$. Semiconductor substrates include silicon (Si) and germanium (Ge) and metal substrates may be, for example, molybdenum (Mo) or tungsten (W). MOCVD has a number of advantages over other deposition techniques, such as sol-gel or physical vapour deposition. MOCMD offers potential for large-area deposition, excellent film uniformity and composition control, high film densities and deposition rates and excellent conformal step coverage at dimensions less than 2 $\mu$m. Furthermore, MOCVD processes are compatible with existing silicon chemical vapour deposition processes used in ULSI and VLSI applications.

Precursors for MOCVD of electro-ceramic the films are generally metal β-diketonates, such as, for example, lead bis-tetramethylheptanedionate (Pb(thd)2, or metal alkoxides. WO 96/40690 discloses various metalorganic complexes of the formula MAyX, wherein M is a y-valent metal, A is a monodentrate or multidentrate organic ligand coordinated to M which allows complexing of MAy with X, y is a integer having a value of 2,3 or 4 and X is a monodentrate, or multidentrate ligand coordinated to M and containing one or more atoms independently selected from C, N, H, S, O and F. A may be a β-diketonate and X may be tetraglyme, tetrahyrofuran, bipyridine, crown ether or thioether.

It is important that the precursors are volatile enough to be transported efficiently at source temperatures which are below the precursor decomposition temperature. In other words, there should be an adequate temperature window between vaporisation and decomposition. The precursors used need to be compatible and not pre-react. They should decompose to form the desired metal oxide in the same temperature region. Ideally, precursors have low toxicity and are stable under ambient conditions.

Available metal alkoxide and metal β-diketonate precursors generally have only very low vapour pressures, so that high source temperatures are required for MOCVD. For example, Pb(thd)2 is typically transported at above 130° C. and Zr(thd)4 at above 166° C. In conventional MOCVD in which a carrier gas is passed through a precursor held at a high temperature for the duration of the deposition process, this can lead to thermal ageing, i.e. decomposition of the precursor prior to transport into the reactor.

One way of avoiding this problem has been to use liquid injection MOCVD, in which a solution of the precursor(s) in an appropriate solvent, e.g. tetrahydrofuran, is evaporated and then transported to the substrate. In this way the precursor is only subjected to heating during evaporation rather than for the duration of the MOCVD process.

For ease of handling and volatility, toxicity and decomposition characteristics, the optimum precursor combination for MOCVD of PZT is Pb(thd)$_2$, Zr(thd)$_4$ and either Ti(OPr$^i$)$_4$ or Ti(OPr$^i$)$_2$(thd)$_2$. However, there is a problem with using Zr(thd)$_4$, in that it is too stable, making it difficult to control the stoichiometry of PZT during liquid delivery MOCVD. In particular, there is a large difference between the decomposition temperature of Zr(thd)$_4$ and the most useful lead precursor Pb(thd)$_2$. This results in a significant difference between the temperatures for diffusion (or mass-limited) oxide film growth between the two precursors and the need to use high substrate temperatures to decompose the Zr(thd), source leads to a loss of lead from the PZT films by evaporation.

Zirconium alkoxides, such as Zr(OPr$^i$)$_4$ and Zr(OBu$^t$)$_4$ are predicted to be much less thermally stable than Zr(thd)$_4$ but are highly air and moisture sensitive making them difficult to manufacture in pure form and too unstable for long term storage.

An object of this invention is to provide alternative Zr precursors for use in MOCVD, especially for depositing PZT and PZLT.

Another object of the invention is to provide an improved method of depositing zirconium containing metal oxides in thin films.

According to a first aspect of this invention there is provided a zirconium precursor suitable for use in MOCVD having the formula $$Zr_x(OR)_yL_z$$

wherein R is an alkyl group

L is a β-diketonate group.

x=1 or 2 y=2, 4 or 6, and z=or 2

According to a second aspect of the invention there is provided a method of depositing thin films of or containing zirconium oxide using metalorganic precursors in an MOCVD technique, wherein the zirconium precursor has the formula $$Zr_x(OR)_yL_z$$

wherein R is an alkyl group

L is a β-diketonate group.

x=1 or 2 y=2, 4 or 6, and z=1 or 2

The preferred alkyl groups R are branched chain alkyl groups, preferably having less than 10 carbon atoms, more preferably having 1 to 6 carbon atoms, especially iso-propyl and tertiary-butyl groups.

The preferred β-diketonate groups L include those of the general formula

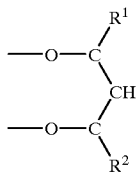

wherein $R^1$ and $R^2$ are the same or different and are straight or branched, optionally substituted, alkyl groups or, optionally substituted, phenyl groups. Examples of suitable substituents include chlorine, fluorine and methoxy.

Examples of suitable β-diketonate groups for use in precursors of the invention include the following:

| $R^1$ | $R^2$ | | |
|---|---|---|---|
| $CH_3$ | $CH_3$ | acetylacetonate | (acac) |
| $CF_3$ | $CH_3$ | trifluoroacetylacetonate | (tfac) |
| $CF_3$ | $CF_3$ | hexafluoroacetylacetonate | (hfac) |
| $CH_3$ | $C(CH)_3$ | dimethylheptanedionate | (dhd) |
| $C(CH)_3$ | $C(CH)_3$ | tetramethylheptanedionate | (thd) |
| $CH_3$ | $CF_2CF_2CF_3$ | heptafluoroheptanedionate | (fhd) |
| $C(CH)_3$ | $CF_2CF_2CF_3$ | heptafluorodimethyloctanedionate | (fod) |
| $CF_2CF_2CF_3$ | $CF_2CF_2CF_3$ | tetradecafluorononanedionate | (tdfnd) |
| $C(CH_3)_3$ | $CF_3$ | trifluorodimethylhexanedionate | (tpm) |
| $CF_3$ | $CF_2CF_3$ | octafluorohexanedionate | (ofhd) |
| $C(CH_3)_3$ | $CF_2CF_3$ | pentafluorodimethylheptanedionate | (ppm) |
| $CF_3$ | $CF_2CF_2CF_3$ | decafluoroheptanedionate | (dfhd) |
| $C(CH_3)_3$ | $CH_2CH_2CH_2OCH_3$ | dimethylmethoxyoctanedionate | (dmmod) |
| $CCL_3$ | $CH_3$ | trichloropentanedionate | (tclac) |
| Ph | Ph | diphenylpropanedionate | (dpp) |

In one preferred embodiment of the invention the zirconium precursor has the following formula:

$Zr(OR)_2L_2$ wherein R and L are as defined above.

Typical examples of such zirconium precursors include $Zr(OPr^i)_2(thd)_2$ and $Zr(OBu^t)_2(thd)_2$ These compounds are believed to be particularly suitable for use in the method according to the invention, especially in liquid injection MOCVD.

In another preferred embodiment of the invention, the zirconium precursor has the following formula:

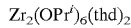
$Zr_2(OPr^i)_6(thd)_2$

Again this compound is believed to be particularly suitable for use in the method of the invention, especially in liquid injection MOCVD.

Compounds of the invention may be produced by reaction of an appropriate zirconium alkoxide with an appropriate β-diketone.

The method of the invention is particularly useful for depositing on a substrate thin films, i.e. in the order of up to 5 μm of lead zirconate titanate (PZT) using a zirconium precursor according to the invention with a lead precursor, such as $Pb(thd)_2$ or lanthanum-modified lead zirconate titanate (PLZT). Typical substrates include $SiO_2$, Si, $SrTiO_3$, MgO, $Al_2O_3$, Ge, Mo and W.

According to a further aspect of the present invention there is provided a method of forming an electro-ceramic device comprising the steps of depositing a lower conducting electrode onto a substrate, depositing a film layer of or containing zirconium oxide onto said electrode and depositing an upper or further conducting electrode thereon, wherein the zirconium oxide layer is formed from the zirconium precursor having the formula:

$Zrx(OR)yLz$ wherein R is an alkyl group;

L is a β-diketonate group;

x=1 or 2;

y=2, 4 or 6; and z=1 or 2.

The lower conducting electrode and upper conducting electrode is preferably a metal, for example, platinum. The substrate is preferably a silicon wafer or circuit. An electro-ceramic device formed by this method is particularly suitable for use in ferro-electric memories and infra-red detectors.

This invention will be further described with reference to the accompanying drawings, in which.

This invention will now be further described by means of the following Examples.

EXAMPLE 1

Preparation of Zirconium di-isopropoxy bis-tetramethylheptanedionate 74 g of tetramethylheptanedionate were dissolved with stiring in 1 liter of hexane in a 2 liter flask.

75 g of zirconium isopropoxide iso-propanol adduct were added to the flask and the mixture brought to reflux for 1 hour. The flask was cooled and the contents filtered through a pad and reduced in volume to dampness using a Buchi roto-evaporator. The residue was redissolved in 300 ml of hexane, clarified through a filter pad, stripped to half volume and 300 ml of dry isopropanol were added. The resultant solution was reduced in volume to 150 ml and set aside to crystallize then filtered off. The crystals were air dried or gently Buchi dried until the odour of isopropanol was removed.

Figure 1:
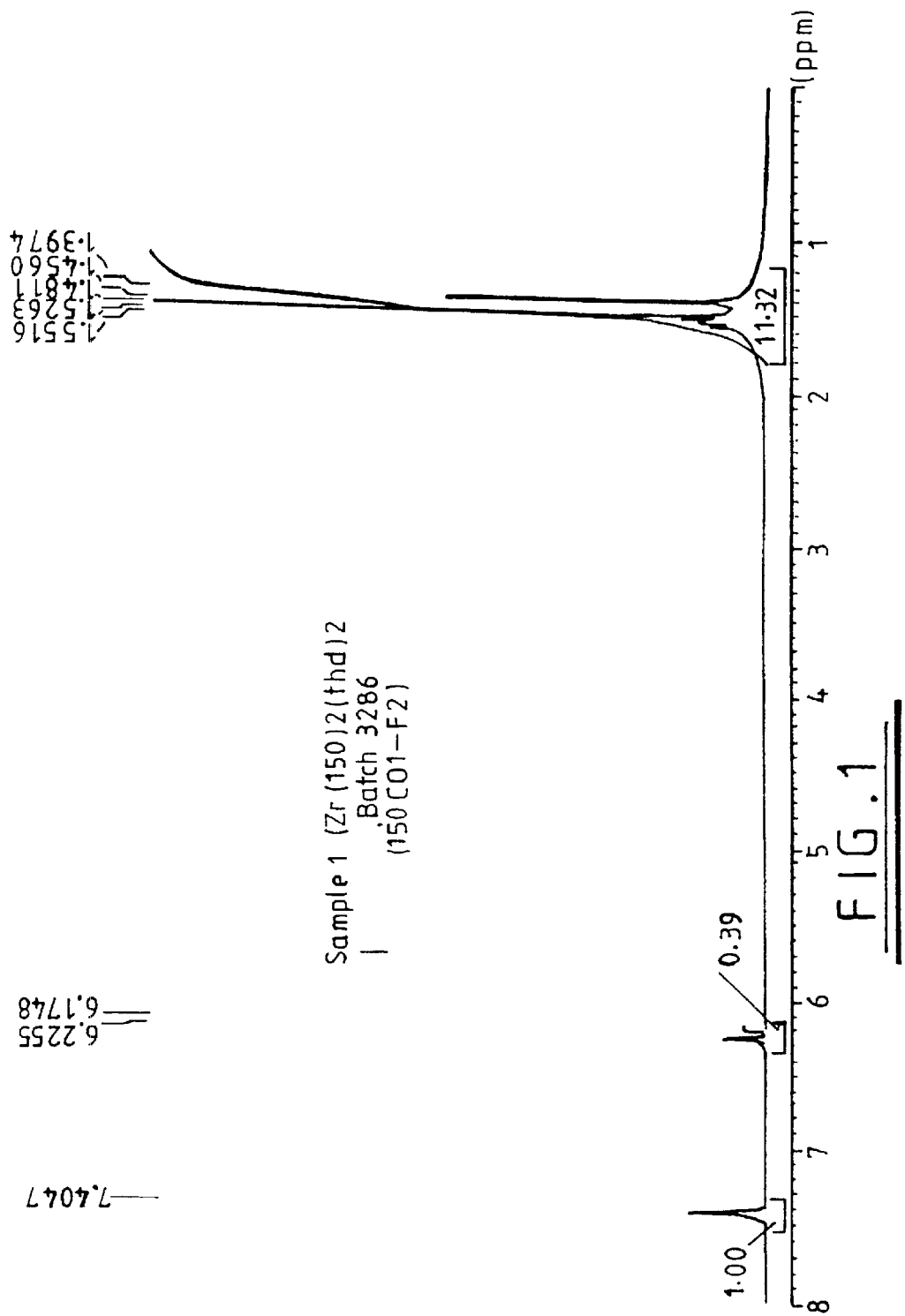
FIG. 1 shows $^1$H NMR spectrum for the product prepared in Example 1 below.
Figure 2:
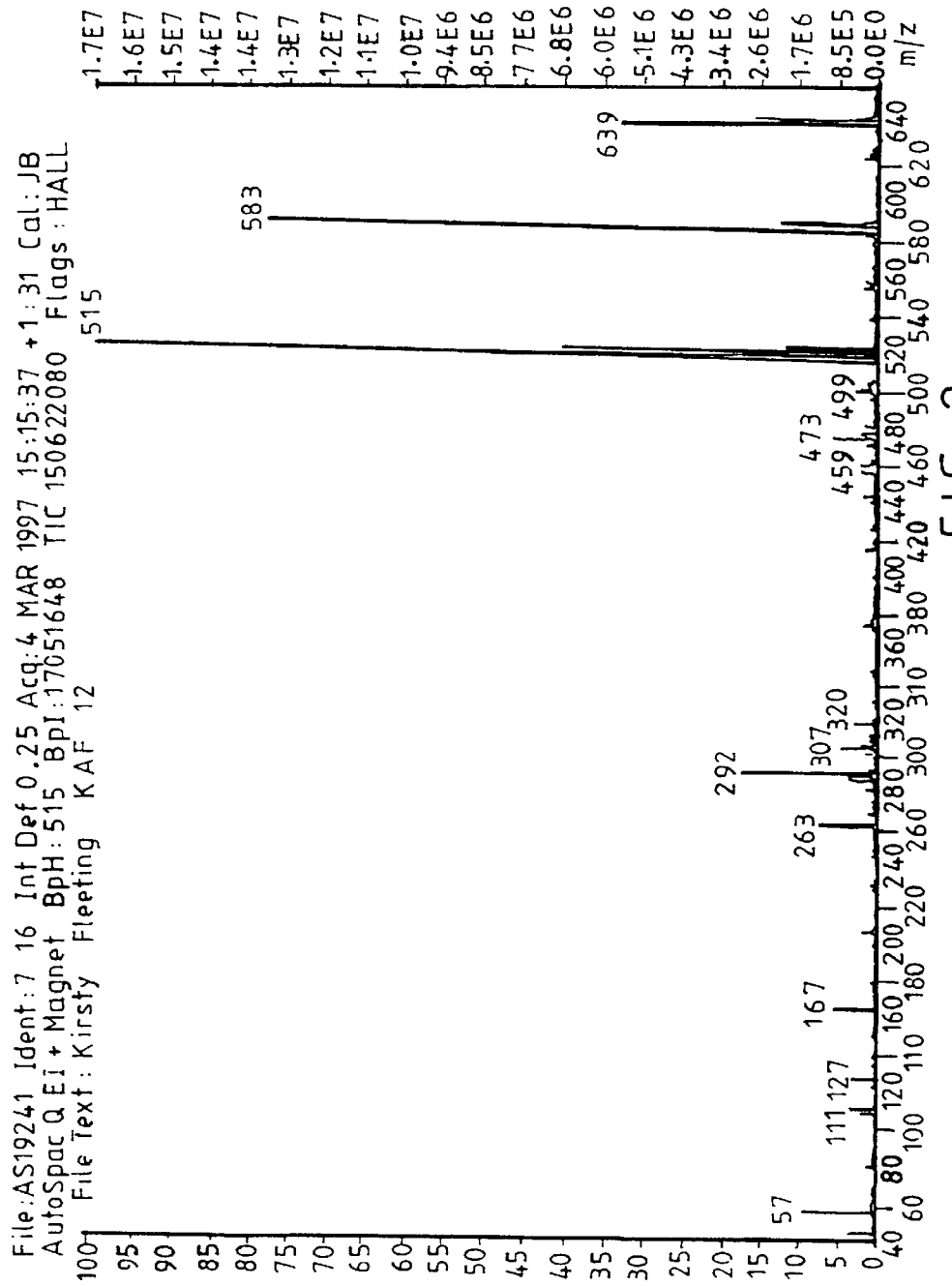
FIG. 2 shows mass spectrometry results for the product prepared in Example 1 below.

The resultant product was relatively air stable, very soluble in hexane and tetrahydrofuran, fairly soluble in ethanol and less in isopropanol. NMR and mass spectral analysis results for the product are shown in FIGS. 1 and 2 of the accompanying drawings respectively and the microanalysis results are as follows:

| Analysis | % C | % H |
| --- | --- | --- |
| Calculated | 58.43 | 9.04 |
| Found | 56.86 | 8.30 |

These results indicate that the product had an approximate stoichiometry of $Zr_2(OPr^i)_2thd_2$.

EXAMPLE 2

Preparation of zirconium di-tertiary-butoxy bis-tetramethylueptanedionate 72 g of tetramethylheptanedione were dissolved with stirring in 1 liter of hexane in a 2 liter flask. 74 g of zirconium tertiary butoxide were added to the flask (a slightly exothermic reaction) and the mixture brought to reflux for 1 hour. The flask was cooled and its contents filtered through a pad before being reduced in volume to 200 ml using a Buchi roto-evaporator and set aside to crystallize. The resulting crystals were filtered off and dried in air or gently Buchi dried till the odour of hexane was removed.

The product was air stable, very soluble in hexane and tetrahydrofuran, fairly soluble in ethanol and less in isopropanol.

Figure 3:
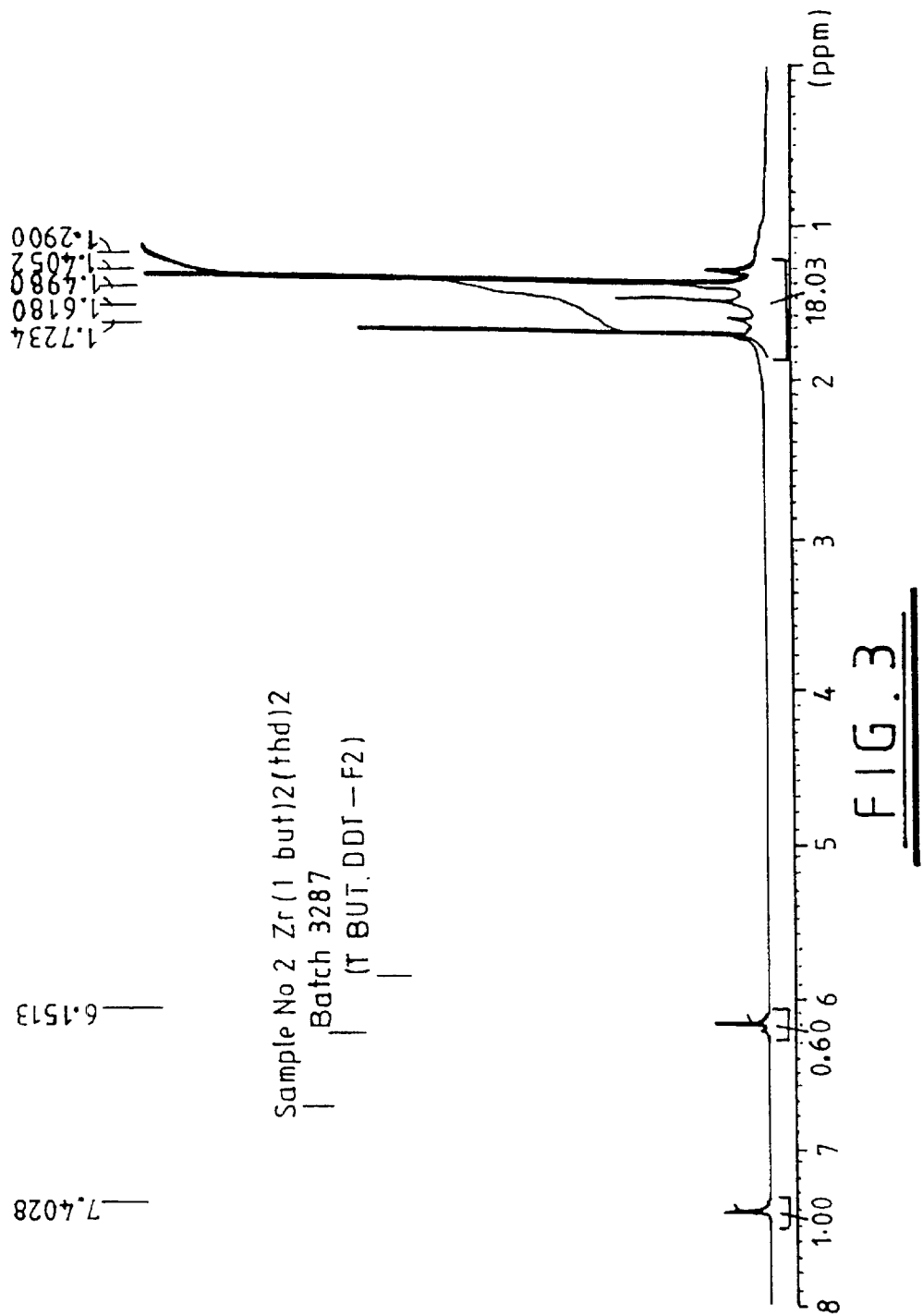
FIG. 3 shows $^1$H NMR spectrum for the product prepared in Example 2 below.
Figure 4:
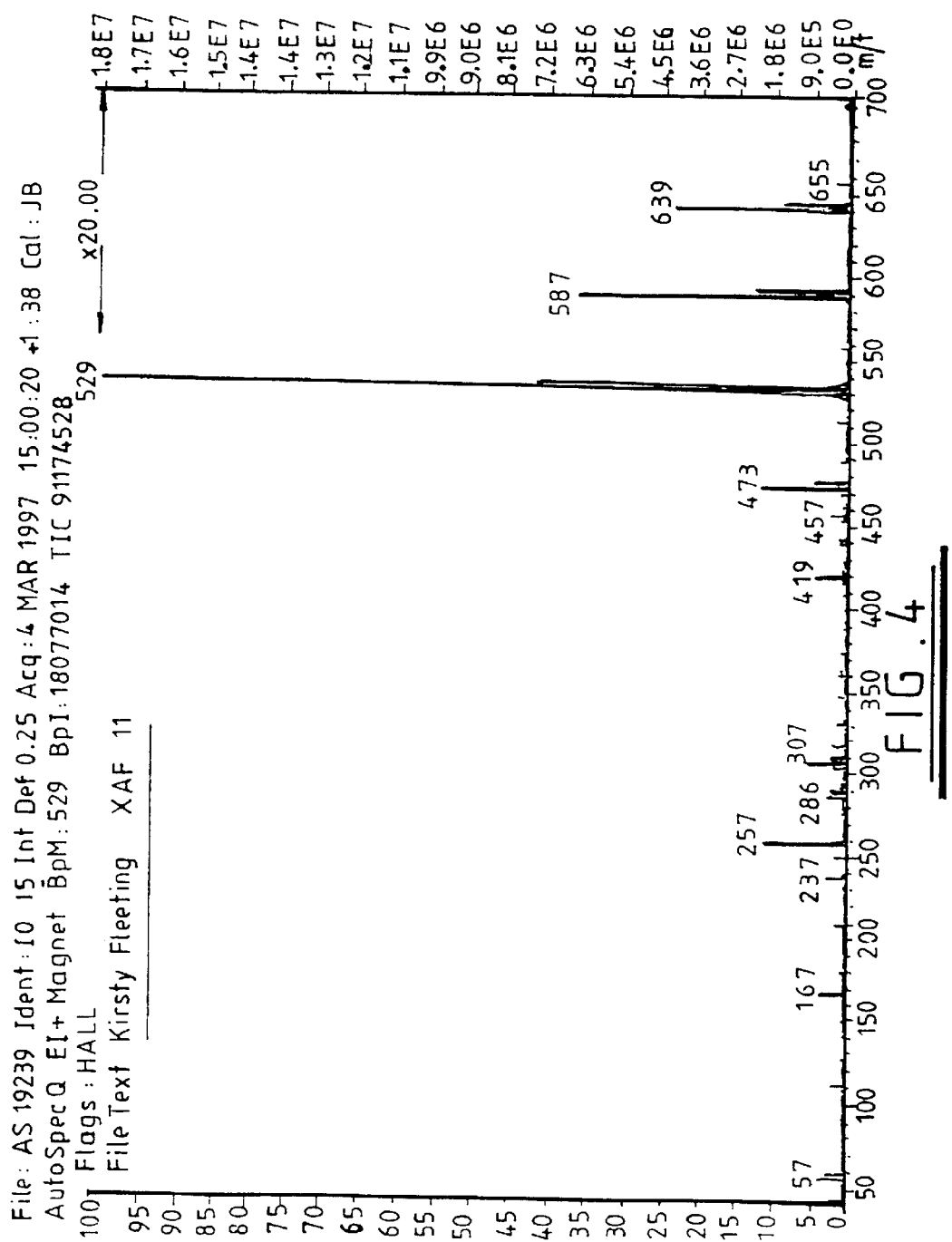
FIG. 4 shows mass spectrometry results for the product prepared in Example 2 below.

NMR and mass spectral analysis results for the product are shown in FIGS. 3 and 4 of the accompanying drawings respectively. The results of the elemental microanalysis are given below:

| Analysis | % C | % H |
| --- | --- | --- |
| Calculated | 59.11 | 9.20 |
| Found | 58.66 | 8.70 |

These results indicate that the product had an approximate stoichiometry of $Zr_2(OBu^t)_2thd_2$.

EXAMPLE 3

Deposition of $ZrO_2$ Thin Films.

Figure 5:
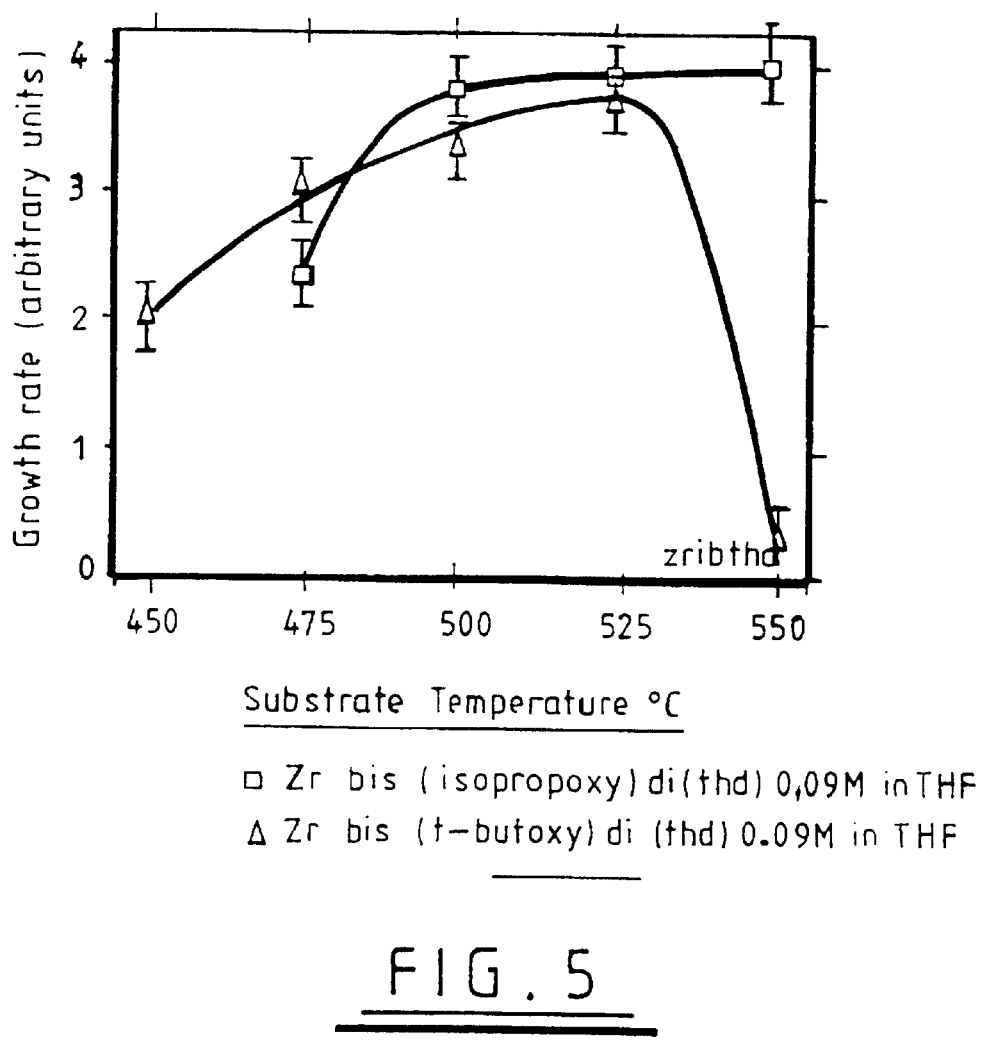
FIG. 5 is a plot of growth rates against substrate temperature achieved by MOCVD using the products of Examples 1 and 2.

Thin films of $ZrO_2$ have been deposited by liquid injection MOCVD with both $Zr(OPr^i)_2(thd)_2$ and $Zr(OBu^t)_2(thd)_2$ in concentrations of 0.09M in tetrahydrofuran. An evaporator temperature of 200° C. was used with argon flow of 4 liters/min and oxygen flow of 100–300 sccm. Growth rates achieved at different substrate temperatures are shown in FIG. 5 of the accompanying drawings.

Figure 6:
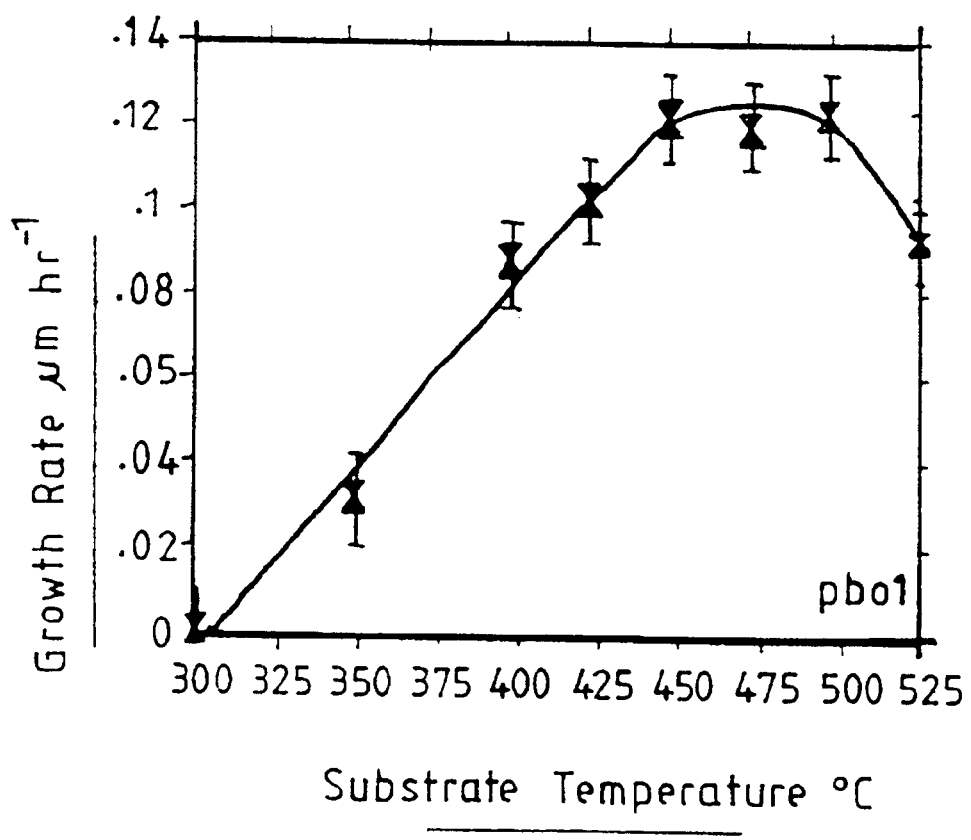
FIG. 6 shows a plot of growth rates against substrate temperature achieved by MOCVD using a lead precursor.

The suitability of either of these $ZrO_2$ precursors for use with a typical lead precursor, such as $Pb(thd)_2$ can be established from FIG. 6 of the accompanying drawings which shows film lead oxide, including $PbO_2$ growth rates from this lead precursor at different substrate temperatures. As can be seen from FIGS. 5 and 6 both the Zr and Pb precursors provide optimum growth rates over a similar range of substrate temperatures, i.e. from about 450–525° C.

It is believed that these Zr precursors are relatively stable to air and moisture due to having six-fold co-ordination around the Zr centre, in contrast to the coordinately unsaturated $Zr(OR)_4$ compounds.

EXAMPLE 4

Figure 7:
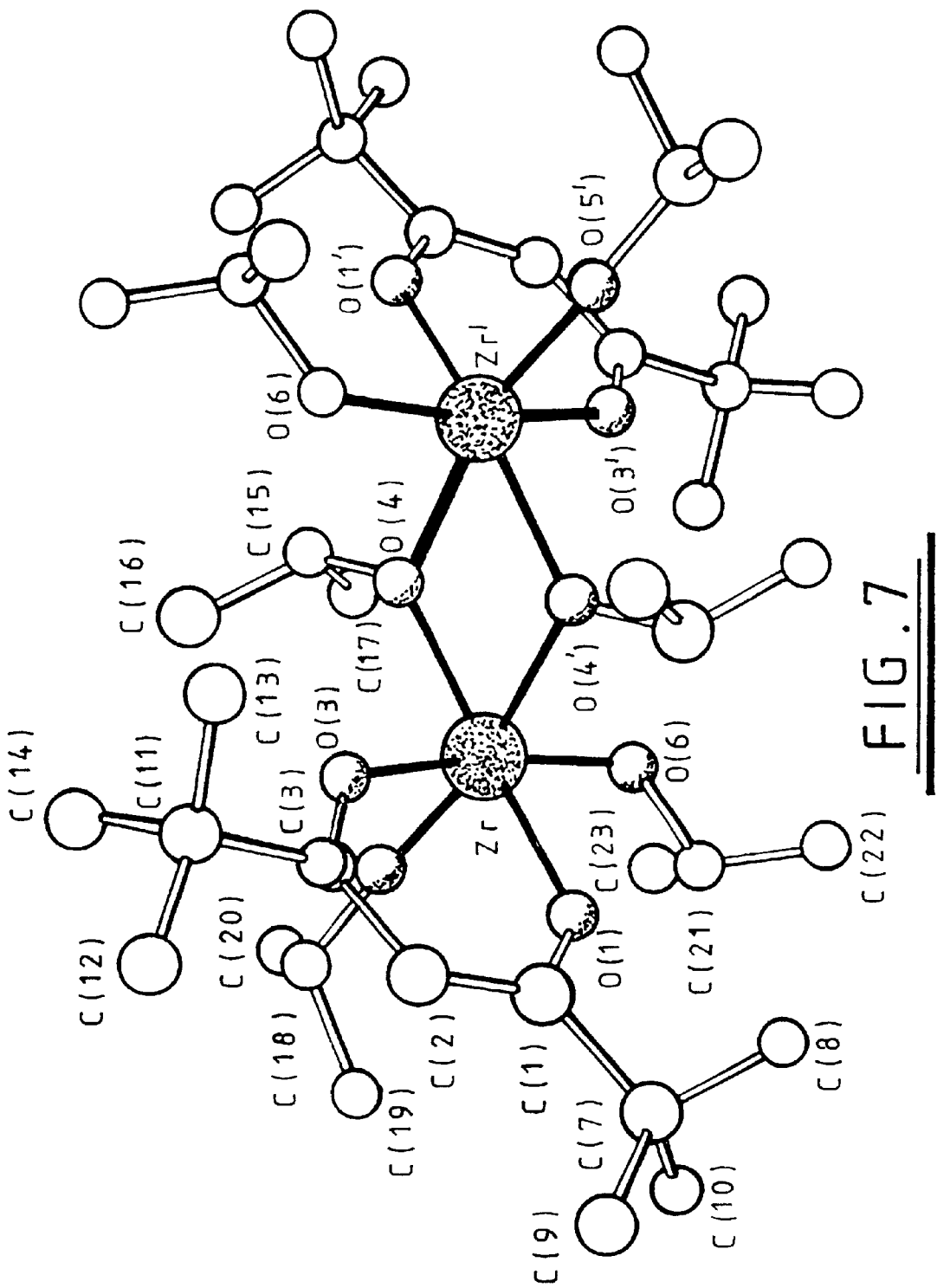
FIG. 7 shows the likely chemical structure of $Zr_2(OPr^i)_6(thd)_2$.

The product from Example 1 was recrystallized from n-hexane. The resultant product had the stoichiometry of $Zr_2(OPr^i)_6(thd)_2$ as shown in FIG. 7 of the accompanying drawings.

EXAMPLE 5

Synthesis of $Zr_2(OPr^i)_6(thd)_2$

Zirconium isopropoxide (2.93 g, 7.56 mmol) was dissolved in toluene (50cm³) and tetramethylheptanedionate (1.58 cm³, 7.56 mmol) was added. The solution was stirred at reflux for 1 hour after which time all volatiles were removed in vacuo to yield a cubite solid. The white solid was re-dissolved in toluene (20 m³) and left to stand at 0° C. overnight. Colourless crystals of $Zr_2(OPr^i)_6(thd)_2$ were filtered off.

EXAMPLE 6

Synthesis of $Zr_2(OPr^i)_6(thd)_2$

Zirconium isopropoxide (2.97 g, 7.25 mmol) was dissolved in n hexane (20 ml) and tetramethylheptane—dionate (3.02 cm³, 14.5 mmol) was added. The solution was stirred at reflux for 1 hour after which time all volatiles were removed in vacuo to yield a white solid. This was re-dissolved in n-hexane (10 cm³) and left to stand overnight. The crystallisation process was repeated four times to yield colourless rhombohedral cyrstals which gave the single ray crystal X-ray structure of $Zr_2(OPr^i)_6(thd)_2$. A proposed chemical structure for $Zr_2(OPr^i)_6(thd)_2$ is shown in FIG. 7 of the accompanying drawings.

$Zr_2(OPr^i)_6(thd)_2$ is believed to be suitable for deposition of thin films of $ZrO_2$ by liquid injection MOCVD.

EXAMPLE 7

Growth Rates Achieved Using the Precursor of Example 6

Figure 8:
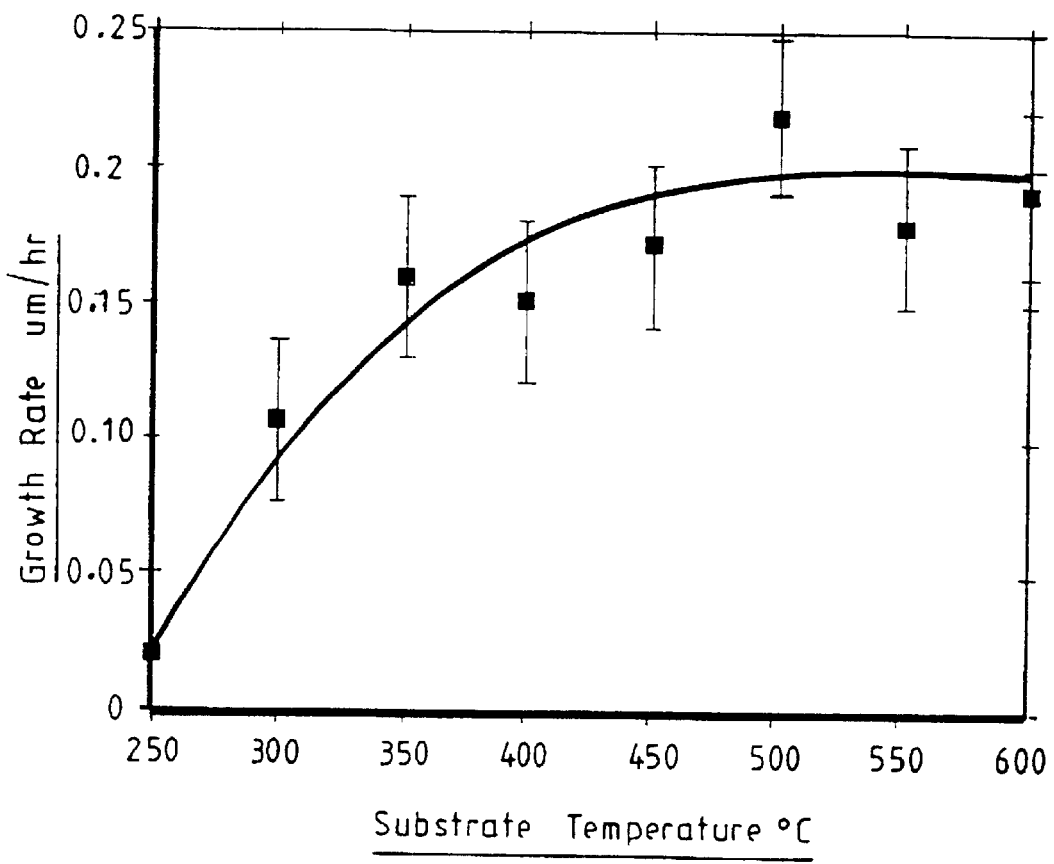
FIG. 8 is a plot of the growth rates against substrate temperature achieved using the precursor $Zr_2(OPr^i)_6(thd)_2$.

$Zr_2(OPr^i)_6(thd)_2$ has proved suitable for the deposition of thin films of $ZrO_2$ by liquid injection MOCVD. The films were grown using a 0.1 molar solution of $Zr_2(OPr^i)_6(thd)_2$ in tetrahydrofuran. An evaporator temperature of 200° C. was used with a precursor injection rate of 3.5 cm³hr⁻¹, an argon flow of 3000–5000 cm³ min⁻¹ and an oxygen flow of 1000–2000cm³ min⁻¹. The growth rates achieved at different substrate temperatures are shown in FIG. 8 of the accompanying drawings, and indicate that $ZrO_2$ growth occurs over a significantly wider temperature range than is achievable with other precursors such as Zr alkoxides or $Zr(thd)_4$.

It is believed that the novel $Zr_2(OPr^i)_6(thd)_2$ source is more suitable than existing Zr precursors for the MOCVD of $Pb(Zr,Ti)O_3$ and related ferro-electric materials at low substrate temperatures and of yttria-stabilised zirconia at more elevated temperatures.

Figure 9:
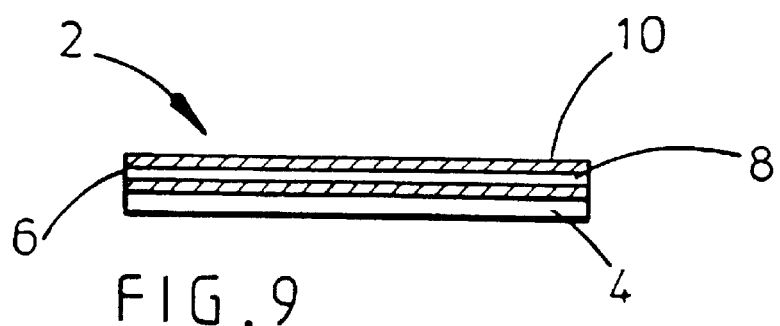
FIG. 9 is a lateral cross-sectional view of an electro-ceramic device according to one embodiment of the present invention.

The zirconium precursors according to the present invention may be used in the preparation of electro-ceramic device 2, as shown in FIG. 9 of the accompanying drawings. A lower conducting electrode 6, such as platinum is deposited onto a substrate 4, such as silicon wafer or circuit and a film layer 8 of a zirconium oxide is formed thereon using the zirconium precursor of the present invention. An upper conducting electrode 10, which may also be platinum, is then deposited onto the zirconium oxide layer by appropriate deposition techniques. The electro-ceramic device may be used, for example, in ferro-electric memories or infra-red detectors, such as those used in security lights.

What is claimed is:

1. A zirconium precursor suitable for use in MOCVD having the formula:

$$Zr_x(OR)_yL_z$$

wherein R is an alkyl group,
L is a β-diketonate group,
x=1 or 2,
y=2, 4 or 6, and
z=1 or 2.

2. A zirconium precursor as claimed in claim 1, wherein R is a branched chain alkyl group.

3. A zirconium precursor as claimed in claim 2, wherein R has less than 10 carbon atoms.

4. A zirconium precursor as claimed in claim 3, wherein R has 1 to 6 carbon atoms.

5. A zirconium precursor as claimed in claim 4, wherein R is selected from isopropyl and tertiary butyl groups.

6. A zirconium precursor as claimed in claim 1, wherein the β-diketonate group L has the following formula:

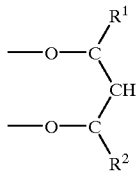

wherein $R^1$ and $R^2$ are the same or different and are selected from straight or branched, optionally substituted, alkyl groups and optionally substituted, phenyl groups.

7. A zirconium precursor as claimed in claim 6, wherein said optional substitaents are selected from chlorine, fluorine and methoxy.

8. A zirconium precursor as claimed in claim 1 having the formula $Zr(OR)_2L_2$.

9. The zirconium precursor $Zr(OP_r^i)_2(thd)_2$, wherein thd is a tetramethylheptanedionate group.

10. The zirconium precursor $Zr(OBu^t)_2(thd)_2$, wherein thd is a tetramethylheptanedionate group.

11. The zirconium precursor $Zr_2(OPr^i)_6(thd)_2$ wherein thd is a tetramethylheptanedionate.

12. A method of depositing on a substrate a thin film comprising or containing a zirconium oxide precursor using a metal organic chemical vapor deposition technique, said process comprising the steps of:

(a) introducing a zirconium precursor into a heated chamber through which gas flows can be controlled to place the zirconium precursor in the gas phase;

(b) transporting the zirconium precursor in the gas phase to a deposition chamber in which a substrate is present; and (c) heating the substrate to a temperature such that decomposition of the zirconium precursor decomposes on the heated substrate thereby depositing the desired oxide thin film wherein the zirconium precursor has the formula:

$$Zr_x(OR)_yL_z$$

in which R is an alkyl group, L is a beta-diketonate group, X is 1 or 2, y is 2, 4 or 6, and Z is 1 or 2.

13. A method as claimed in claim 12, wherein one of the precursors is a lead precursor.

14. A method as claimed in claim 13, wherein the lead precursor is $Pb(thd)_2$.

15. A method as claimed in claim 12, wherein the substrate is selected from $SiO_2$, Si, $SrTiO_3$, MgO, $Al_2O_3$, Ge, Mo and W.

16. A method of forming an electro-ceramic device comprising the steps of depositing a lower conducting electrode onto a substrate, depositing a film layer of or containing zirconium oxide onto said electrode and depositing an upper or further conducting electrode thereon wherein the zirconium oxide layer is formed from a zirconium precursor as claimed in claim 1.

17. A method as claimed in claim 16, wherein the lower and/or upper conducting electrode is a metal.

18. A method as claimed in claim 17, wherein the metal is platinum.

19. A method as claimed in claim 16, wherein the substrate is selected from a silicon wafer or circuit.

20. An electroceramic device formed by the method of claim 16.

21. An electro-ceramic device as claimed in claim 20 for use in ferro-electric memories.

22. An electro-ceramic device as claimed in claim 20 for use in an infra-red detector.

* * * * *